United States Patent [19]

Hagiwara et al.

[11] Patent Number: 5,155,036
[45] Date of Patent: Oct. 13, 1992

[54] SERUM-FREE MEDIUM CONTAINING RETINOIC ACID USEFUL FOR CULTIVATING HUMAN/HUMAN HYBRIDOMAS

[75] Inventors: Hideaki Hagiwara; Masafumi Naito; Hideo Yuasa, all of Kasai, Japan

[73] Assignees: Yoshihide Hagiwara; Hideaki Hagiwara, both of Hyogo, Japan

[21] Appl. No.: 230,973

[22] Filed: Aug. 11, 1988

[30] Foreign Application Priority Data

Aug. 21, 1987 [JP] Japan ................................ 62-206,569

[51] Int. Cl.$^5$ ..................... C12N 5/00; C12N 15/00; A61K 35/14; C12P 21/02
[52] U.S. Cl. ............................ 435/240.27; 435/70.21; 435/240.31; 530/388.15; 530/865; 935/99; 935/100
[58] Field of Search ........... 435/240.3, 240.31, 240.27, 435/240.25, 240.26, 70.2; 935/99; 530/387

[56] References Cited

U.S. PATENT DOCUMENTS 4,205,126 5/1980 Cartaya .................................... 435/2

OTHER PUBLICATIONS

Muakami et al. Human-Human Hybridomas Secreting Antibodies Specific to Human Lung Carcinoma; In Vitro Cellular & Developmental Biology v. 21, No. 10 pp. 593-596 1985.
Rodrigues et al. Exp. Cell Research 156 (1985) 22-30.
Barnes & Sato Analytical Biochemistry 102 255-270 (1980).
Journal of Immunological Methods, vol. 57, 1983, pp. 121-136, "Automated Production of Monoclonal Antibodies in a Cytostat" by S. Fazekas de St. Groth.
Chemical Abstracts, vol. 97, 1982, p. 365, Abstract No. 159112n, "Clonal Growth of Normal Adult Human Bronchial Epithelial Cells in a Serum-Free Medium".
Biological Abstracts, vol. 79, 1985, Abstract No. 22483, "Immunological aspects of retinoids in humans: 2. Retinoic acid enhances induction of hemolytic plaque--forming cells".
Chemical Abstracts, vol. 103, 1985, p. 575, abstract no. 121561n, "Potentiation of Mitogen-Induced human T-lymphocyte activation by retinoic acid".
"Monoclonal Antibodies: Production and Application (Advances in Biotechnological Processes, vol. II)", Mizrahi.
"Enhancing Effects of Retinoic Acid on Monoclonal Antibody Production of Human-Human Hybridomas", Cellular Immonology I33, 498-505 (1991) Aotsuka and Naito.

Primary Examiner—Douglas W. Robinson
Assistant Examiner—Jane A. Williams
Attorney, Agent, or Firm—Sherman and Shalloway

[57] ABSTRACT

A serum-free medium for cultivating a human monoclonal antibody-producing human/human hybridoma, said medium comprising a serum-free complete medium and at least $10^{-12}$ M but not more than $10^{-6}$ M of retinoic acid or its salt.

16 Claims, 2 Drawing Sheets

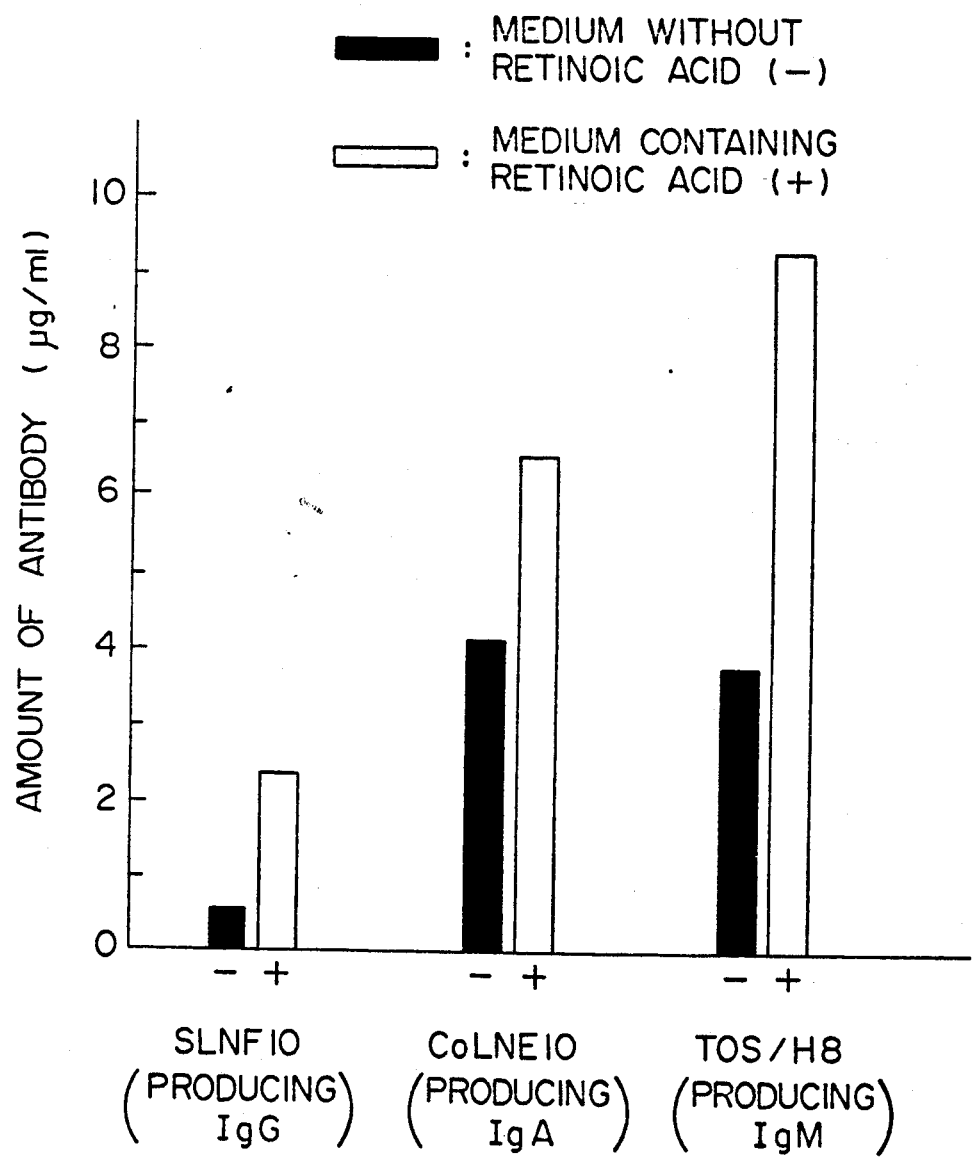

SERUM-FREE MEDIUM CONTAINING RETINOIC ACID USEFUL FOR CULTIVATING HUMAN/HUMAN HYBRIDOMAS

This invention relates to a serum-free medium useful for cultivating a human monoclonal antibody-producing human/human hybridoma, for example in the analysis of biochemical mechanisms and the production of bio-products useful for diagnostic, prophylactic and therapeutic purposes in the field of biotechnology. More specifically, it relates to a serum-free medium for cultivating a human monoclonal antibody-producing human/human hybridoma, in which the human/human hybridoma can be cultivated to give a human monoclonal antibody in a markedly improved output and subcultivation suitable for industrial practice can be carried out.

More specifically, it relates to a serum-free medium for cultivating a human monoclonal antibody-producing human/human hybridoma, comprising a serum-free complete medium and at least $10^{-12}$M but not more than $10^{-6}$M, preferably at least $10^{-10}$M but not more than $10^{-6}$M, more preferably at least $10^{-9}$M but not more than $10^{-7}$M, of a retinoic acid or its salt.

A number of basal media (media not containing serous components such as serum or serum albumin), for example basal media for animal cell cultivation have been known, and as many as about 50 basal media are commercially available. In the cultivation of animal cells, it is the usual practice to use them as complete media by adding proper amounts, for example about 5 to 10% (vol/vol-medium), of serum such as calf serum or human serum to these basal media in order to maintain growth and proliferating ability of the cells at practical levels.

Serum, however, contains a variety of foreign heterogeneous factors including high-density lipolipid (HDL) and low density lipolipid (LDL), and the inclusion of such undesirable heterogenous factors in the media cannot be avoided. The use of serum-containing complete media in the analysis of biochemical mechanisms such as the cell proliferation mechanism and the antibody production mechanism or in the production of bio-products such as antibodies or other useful substances causes various technical troubles. For example, the analysis of biochemical mechanism is impeded, or highly pure useful bio-substances of high quality free from inclusion of hetrogeneous factors from the serum added to the media cannot be obtained easily.

To avoid such troubles, it is desired to cultivate animal cells in a serum-free medium. Usually, the use of such serum-free medium adversely affects the growth, proliferation and antibody production of cells cultivated, or makes subcultivation desirable for industrial practice virtually impossible. The deleterious effects of a variety of mixed heterogeneous factors derived from serum cause a more serious technical trouble in the cultivation of a human monoclonal antibody-producing human/human hybridoma.

One of the inventors of the present application unexpectedly discovered that by including an amino acid component in a considerably higher concentration than those of amino acids previously used commonly, particularly a specific high concentration of L-arginine, as at least one amino acid component, there can be provided a true serum-free complete medium which does not contain serum and/or serum albumin and which maintains the growth, proliferation and antibody production ability of a human/human hybridoma, and is thus free from the deleterious effects of foreign factors derived from serum and/or serum albumin. The invention based on this discovery was applied for a patent in Japanese Patent Application No. 192145/1985 (Japanese Laid-Open Patent Publication No. 51983/1987). This patent document, however, fails to disclose the incorporation of retinoic acid in the serum-free complete medium, and further fails to describe and suggest any effects of retinoic acid on the cultivation of a human/human hybridoma in the above medium.

Some papers have previously been published on cell cultivation using a medium containing retinoic acid (also known as vitamin A acid) of the following formula:

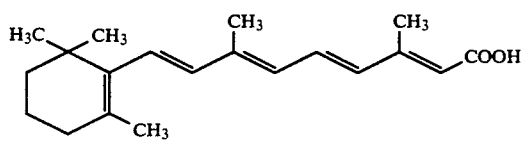

For example, Frank H., Valone, and Donald G. Payan, "Cancer Research", 45, 4128–4131 (1985) states that in a serum-containing medium containing $5 \times 10^{-6}$M of retinoic acid, the proliferation of human B lymphocytes purified from a human blood sample was inhibited. It only describes a negative finding on the utilization of retinoic acid, and does not at all describe the effect of retinoic acid on a serum-free medium and the effect of retinoic acid on the cultivation of a human/human hybridoma. This paper neither describes nor suggests the effect of retinoic acid on the antibody production of human B lymphocytes in a serum-containing medium containing $5 \times 10^{-6}$M of retinoic acid.

Neil Sidell et al., "Cellular Immunology", 88, 374–381 (1984) reported than differentiation of B lymphocytes into antibody-producing cells was promoted by cultivating tonsil lymphocytes in a serum-containing medium containing retinoic acid in a concentration of $10^{-7}$M, $10^{-6}$M and $10^{-5}$M together with an antigen, or by cultivating human B lymphocytes purified from tonsil lymphocytes in a serum-containing medium containing $10^{-5}$M of retinoic acid together with an antigen. This paper neither refers to any finding on a serum-free medium, nor does it disclose any effect of retinoic acid on the cultivation of a human/human hybridoma. The paper does not at all describe nor suggest the effect of retinoic acid on antibody-producing cells already differentiated, particularly its effect on the antibody-producing ability of these cells.

As stated above, these prior literature references disclose only serum-containing media which further contain retinoic acid, and do not at all describe the action and effect of retinoic acid in a serum-free medium. Furthermore, these references neither describe nor suggest any finding which may anticipate the effect of retinoic acid on the growth, proliferation and antibody-producing ability of a human monoclonal antibody-producing human/human hybridoma.

Thus, the utilization of retinoic acid or its salt as a component of a serum-free medium and its behavior in the cultivation of a human monoclonal antibody-producing human/human hybridoma have been completely unknown in the past.

The present inventors furthered their investigations on the development of a serum-free complete medium suitable for culturing a human/human hybridoma, particularly a monoclonal antibody-producing human/human hybridoma.

In the present invention, the serum-free complete medium denotes a complete medium which does not contain serum. If desired, however, serum albumin may be added to it.

These investigators have led to the discovery that a serum-free culture medium prepared by adding retinoic acid or its salt in a concentration of at least $10^{-12}$M but not more than $10^{-6}$M to a serum-free complete medium is suitable for cultivating a human monoclonal antibody-producing human/human hybridoma, markedly increases the antibody-producing ability of the human-human hybridoma, and makes it possible to perform sub-cultivation of the hybridoma smoothly on an industrial scale.

Investigators of the present inventors have shown that as FIG. 1 of the accompanying drawings gives one example, the content of retinoic acid in the serum-free complete medium containing retinoic acid shows a considerably critical tendency, and that the amount of a monoclonal antibody produced by the monoclonal antibody-producing human/human hybridoma in the medium of this invention increases abruptly with a retinoic acid content of about $10^{-10}$M to $10^{-9}$M, reaches a maximum with a retinoic acid content of about $10^{-8}$M to $10^{-7}$M, and abruptly decreases when it exceeds $10^{-6}$M.

In a preferred embodiment of this invention, a serum-free complete medium composed of a basal medium for animal cell cultivation and at least one growth factor selected from insulin and transferrin and being free from serum can be widely used. By including retinoic acid in a concentration of at least $10^{-12}$M but not more than $10^{-6}$M, preferably at least $10^{-10}$M but not more than $10^{-6}$M, more preferably at least $10^{-9}$M but not more than $10^{-7}$M in this serum-free complete medium, a serum free medium for culturing a human monoclonal antibody-producing human/human hybridoma can be provided.

It is an object of this invention therefore to provide a serum-free medium for cultivating a human monoclonal antibody-producing human/human hybridoma.

The above and other objects and advantages of this invention will become more apparent from the following description.

The serum-free medium for cultivating a human monoclonal antibody-producing human/human hybridoma in accordance with this invention contains at least $10^{-12}$M but not more than $10^{-6}$M of retinoic acid or its salt in the serum-free complete medium.

The serum-free complete medium is used in this invention may be a serum-free complete medium composed of any one of known and commercially available basal media (media not containing serous components such as serum or serum albumin) and at least one growth factor. A preferred example of such a serum-free complete medium is a serum-free complete medium composed of a known commercially available basal medium for cultivating animal cells and at least one growth factor selected from the group consisting of insulin and transferrin and being free from serum.

The serum-free complete medium may contain complete medium-forming additives (meant to exclude serum in this invention) which can be used to form a complete medium by addition to a basal medium in addition to insulin and/or transferrin. Examples of the complete medium-forming additives include β-mercaptoethanol, selenites such as Na or K selenite, ethanolamine, L-arginine, albumin, other known amino acids, vitamins, minerals, nucleic acid derivatives, carbohydrates, coenzymes and fatty acids for culture media. They may be used in suitable combinations.

Some examples of the serum-free complete medium are given below.

For example, there may be cited a serum-free medium comprising a complete medium for animal cell culture (disclosed in Japanese Laid-Open Patent Publication No. 51983/1987 filed by the same applicants as the present application) containing (1) a basal medium for animal cell culture,
(2) at least one growth factor selected from the group consisting of insulin and transferrin,
(3) ethanolamine,
(4) mercaptoethanol, and
(5) a selenite (such as Na or K selenite), and further
(6) L-arginine in a high concentration of more than about 1000 mg/liter-complete medium but not more than about 45,000 mg/liter-complete medium, as essential components, and a serum-free medium of the above composition except that it contains about 0.1 to about 1 mg/ml-complete medium of (7)serum albumin further or instead of L-arginine (6).

A serum-free medium composed essentially of the above components (1), (2), (4), (5) and (6), a serum-free medium composed essentially of the above components (1), (2), (4), (5) and (7), a serum-free medium composed essentially of the above components (1), (2), (4) and (5), and a serum-free medium composed essentially of the above components (1), (2) and (5) may also be used in this invention by including a specific amount of retinoic acid or its salt.

The amounts of the components (2) to (7) to be added to the basal medium (1) may be properly varied with the types of these essential components, the combination thereof, the purpose of cultivation, and the type of the human/human hybridoma to be cultivated, and cannot be generalized. Those skilled in the art, however, can easily determine preferred amounts experimentally according to these factors. In the case of the above serum-free complete medium containing (1) to (6) as essential components, the amounts may be, for example, about 2 to 50 mg for the component (2), about $10^{-8}$ to $10^{-4}$ mole for the component (3), about $10^{-8}$ to $10^{-4}$ mole for the component (4) and about $10^{-11}$ to $10^{-7}$ mole for the component (5), all per liter of the complete medium.

Various examples of the basal medium (1) for animal cell culture are known and can be prepared in accordance with the known literature (for example, "Cell Culture Manual", 3rd edition, Jul. 20, 1984, published by Kodansha Scientific). Many of them are commercially available, and can be utilized in this invention.

Examples of such a basal medium include known basal media and known modified media thereof shown below.

BME medium (Basal Medium Eagle) described, for example, in Eagle, H.: Science, 122, 501 (1955); Eagle, H.: J. Exp. Med., 102, 37 (1955) and 102, 595 (1955); Eagle, H.: J. Biol. Chem., 214, 839 (1955); Eagle, H. et al.: Science, 123, 845 (1955); Hanks, J. H., Wallace, R. E.: Proc. Soc. Exp. Biol. Med., 71, 196 (1949); Yamane, I.: Proc. Soc. Exp. Biol. Med., 127, 335 (1968); Morton, H. J.: In Vitro, 6, 89 (1970); and Eagle, H.: Proc. Soc. Exp. Biol. Med., 89, 362 (1955).

MEM medium (Minimum Essential Medium) described, for example, in Eagle, H.: Science, 130, 432 (1959); Stoker, M., MacPherson, I.: Virology, 14, 359 (1931); MacPherson, I., Stoker, M.: Virology, 16, 147 (1962); Stoker, M., MacPherson, I.: Nature, 203, 1355 (1964); Dulbecco, R., Freeman, G.: Virology, 8, 396 (1959); Smith J. d., et al.: Virology, 12, 185 (1960); Stanners, C. P. et al.: Nature New Biology, 230, 52 (1971); and Stanners, C. P., Stewart, C.: Personal Communication (1972).

199 Medium described, for example, in Morgan J. F. et al.: J. Nat. Cancer Inst., 16, 557 (1955); and Morton H. J.: In Vitro, 6, 89 (1970).

L-15 Medium described, for example, in Leibvitz, A.: Amer. J. Hyg., 78, 173 (1963).

Ham's Medium described, for example, in Ham, R. G.: Exp. Cell Res., 29, 515 (1963); Ham, R. G.: Proc. Nat. Acad. Sci., 53, 288 (1965); and Morton, H. J.: In Vitro, 6, 89 (1970).

McCoy 5A medium described, for example, in Neuman, R. E., McCoy, T. A.: Proc. Exp. Biol. Med., 98, 303 (1958); McCoy, T. A., et al.: Proc. Exp. Biol. Med., 100, 115 (1959); and Hsu, T. C., Kellogg, D. S.: J. Nat. Cancer Inst., 25, 221 (1960).

RPMI Medium described, for example, in Moore, G. E. et al.: J. A. M. A., 199, 519 (1967), and Moore, G. E. et al: J. Nat. Cancer Inst., 36, 405 (1966).

Williams' Medium E described, for example, in Williams, G. M., Weisburger, E. K. and Weisburger, J. H.: Exp. Cell Res., 69, 106–112 (1971).

NCTC 135 Medium described, for example, in Evans, V. J. et al.: Exp. Cell Res., 36, 439 (1968).

Waymouth's Medium MB752/1 described, for example, in Waymouth, C: J. Nat. Cancer Inst., 22, 1003 (1959), and Morton, H. J.: In Vitro, 6, 89 (1970).

The above exemplified basal media for animal cell culture may be used singly or as mixtures in suitable proportions.

The serum-free medium of this invention for cultivating a human monoclonal antibody-producing human/human hybridoma is composed of such a serum-free complete medium as illustrated above and at least $10^{-12}M$ but not more than $10^{-6}M$ of retinoic acid or its salt.

The amount of retinoic acid or its salt may be properly varied within the above range depending upon various factors such as the types of the basal medium constituting the serum-free complete medium and the complete medium-forming additives, their combinations and proportions, the type of the human/human hybridoma to be cultivated and the purpose of cultivation. Those skilled in the art, if required, can select and determine preferred amounts of retinoic acid or its salt according to these factors. The preferred amount is, for example, at least $10^{-10}M$ but not more than $10^{-6}M$, especially at least $10^{-9}M$ but not more than $10^{-7}M$. In view of the balance between the increase of the number of cells and the output of an antibody in subcultivation in industrial practice, the especially preferred amount of retinoic acid or its salt is, for example, at least $10^{-9}M$ but less than $10^{-7}M$. The output of the antibody tends to decrease considerably if the content of retinoic acid or its salt is smaller or larger beyond the above-specified range.

There is no particular restriction on the human monoclonal antibody-producing human/human hybridoma to be cultivated by using the serum-free medium of the invention containing retinoic acid or its salt. The serum-free medium of this invention may be used to cultivate any human/human hybridoma having the ability to produce a human monoclonal antibody.

The human/human hybridoma and the method of its formation are not the subject matter of this invention. Some examples of such hybridomas include the human monoclonal antibody-producing human/human hybridomas disclosed in Japanese Laid-Open Patent Publication Nos. 201994/1983, 13589/1984, 137497/1984, and 70400/1987 which can be obtained by the methods disclosed in these patent documents; and the human monoclonal antibody-producing human/human hybridomas disclosed in detail in Japanese Laid-Open Patent Publication Nos. 155083/1987 and Japanese Patent Application Nos. 202752/1986 filed on Aug. 30, 1986, and 126687/1987 filed on May 23, 1987 which can be obtained by utilizing the techniques disclosed in the first four Japanese Laid-Open Patent Publications cited above.

Specific examples of these human/human hybridomas are human/human hybridoma CLN/SUZH5 (Fermentation Research Institute, Deposition Rejecting Notice No. 57-637), human/human hybridoma CLN H5 (ATCC HB8206) and human/human hybridoma SLN F10 (Fermentation Research Institute, Deposition Rejecting Notice No. 60-1197), which are disclosed in the above-cited patent documents; human/human hybridoma CoLNE10 (Fermentation Research Institute, Deposition Rejecting Notice No. 61-794) which can be obtained by the same techniques as disclosed in the above patent documents except that human B-cell derived from a patient with cancer of the colon was used; human/human hybridoma TOS/G5 (Fermentation Research Institute, Deposition Rejecting Notice No. 60-1197), which are disclosed in the above-cited patent documents; human/human hybridoma CoLNE10 (Fermentation Research Institute, Deposition Rejecting Notice No. 61-794) which can be obtained by the same techniques as disclosed in the above patent documents except that human B-cell derived from a patient with cancer of the colon was used; human/human hybridoma TOS/G5 (Fermentation Research Institute, Deposition Rejecting Notice No. 60-1196); TOS/H8 (Fermentation Research Institute, Deposition Rejecting Notice No. 61-844) of human B-cell derived from a patient with stomach cancer and human B cell lymphoblast cell mutant HIH/TO1 (Fermentation Research Institute, Deposition Rejecting Notice No. 60-1198) as a fusion partner disclosed in detail in Japanese Laid-Open Patent Publication No. 155083/1987 cited above and summarized hereinbelow; human/human hybridoma TOH/B9 (Fermentation Research Institute, Deposition Rejecting Notice No. 62-5); TOH/D5 (Fermentation Research Institute, Deposition Rejecting Notice No. 62-6; and TOH/G2 (Fermentation Research Institute, Deposition Rejecting Notice No. 62-7) formed from the aforesaid fusion partner and human B-cell derived from a patient with liver cancer.

The formation of fusion partners typified as HIH/TO1 given as a typical example of fusion partner above and the techniques of forming human/human hybridomas using them will be described below briefly although they are not the subject matter of the present invention.

The above fusion partner can be obtained from human B cell lymphoblast cells W1-L2 (Fermentation Research Institute, Deposition Rejecting Notice No. 60-1621) by a mutant forming operation in accordance with a technique of making it drug-resistant. The resulting cell line having self-replicability is a mutant derived from human B cell lymphoblast cells and has the following characteristics (i) to (v).

(i) It is resistant to 6-thioguanine.
(ii) It is resistant to ouabain.
(iii) It dies in a medium containing HATO (hypoxanthine, amethopterin, thymidine and ouabain).
(iv) It does not substantially produce immunoglobulins IgG and IgM.
(v) It can replicate in a serum-free medium composed of basal medium RDF and insulin, transferrin, selenium, ethanolamine, $\beta$-mercaptoethanol and bovine serum albumin.

More specifically, the above fusion partner which is a human B cell lymphoblast cell mutant can be created by, for example, cultivating and adapting human B cell lymphoblast cells in a serum-free medium, screening the adapted cells to select cells substantially lacking the ability to product immunoglobulins, cultivating and adapting the selected cells in a 6-thioguanine-containing serum-free medium, treating the resulting 6-thioguanine-resistant cells with a mutating agent, cultivating and adapting the treated cells in an ouabain-containing serum-free medium, and cloning the resistant cells in a serum-free medium containing both 6-thioguanine and ouabain.

A preferred example of the serum-free medium used at this time is a serum-free medium prepared by adding suitable amounts of insulin, transferrin, selenium, ethanolamine, $\beta$-mercaptoethanol and bovine serum albumin to basal medium RDF (a mixture of RPMI 1640, DME and F12 in a ratio of 2:1:1). Other serum-free media may also be used, and they may be experimentally selected, changed or determined according to the types of the human B cell lymphoblast cells to be cultivated and the basal medium, the types and amounts of the additives to the basal medium, etc. Examples of the mutating agent include known ones such as MNNG, EMS, AAB, AAF, AF-2, $BP_{0x}$, DAB, BZD, DAN, DBA, DBE, DBP, DMN, ENNG, ENU, HFA, 3MCA, MMS, 2NA, NAAAF, NBA, 4NQO, OAT, PI, TCE, TDS, TOX and VC.

The cultivation and adaptation may be carried out, for example, at 37° C. in the presence of 5% $CO_2$. Cloning may be carried out by a known method, for example by a limiting dilution method. Known cultivation and adaptation means, screening means and means of treating with mutating agents may be properly used.

Examples of the human B cell lymphoblast cells include the above human B cell lymphoblast cells WI-L2 and other known cell lines such as human B cell lymphoblast cells IM-9 (ATCC CCL 159), human B cell lymphoblast cells NC-37 (ATCC CCL 214) and human B cell lymphoblast cells CCRF-SB (ATCC CCL 120).

A human monoclonal antibody-producing human/human hybridoma which makes it possible to produce an antigen-specific human immunoglobulin industrially outside the human body may be created, for example, by fusing human lymphocyte cells (human B cells) taken from a patient with a malignant tumor with the fusion partner described above.

The fusion operation for producing such fused cells is well known. Fusion can be carried out, for example by contacting human B cells of a cancer patient with a mutant of human B cell lymphoblast cells as a fusion partner in a liquid medium in the presence of a fusion promotor such as Sendai virus (HVJ) or polyethylene glycol. It can also be carried out electrically at a high voltage (for example, U. Zimmerman et al.: "Electric Field-Mediated Cell Fusion", The Journal of Biological Physics, 10, 43–50, 1982; U. Zimmerman et al.: "Electric Field-Induced Cell-to-Cell Fusion", The Journal of Membrane Biology, 67, 165–182, 1982; and U. Zimmerman, "Electric Field-Mediated Fusion and Related Electrical Phenomena", Biochimica et Biophysica Acta, 694, 27–277, 1982).

In the first-mentioned embodiment, the human B cells from a cancer patient and the human B cell lymphoblast cells as the fusion partner are contacted for a period sufficient to produce fusion cells, for example, for several minutes, in an aqueous medium in the presence of the fusion promotor, if desired while the system is gently stirred to make it homogeneous. Examples of the aqueous medium are water, physiological saline, a 5% aqueous solution of dimethyl sulfoxide and a 5% aqueous solution of glycerol.

The fusion system in which the desired fusion cells have thus been produced is centrifuged to harvest the fused cells. The fused cells are then dispersed in a suitable medium, for example, an RDF basal medium supplemented with 10% calf serum and HATO. The dispersion is injected into the wells of a microliter plate in fixed amounts, and the plate is incubated, for example in the presence of 5% $CO_2$ at 37° for a period of, for example, 2 weeks while the culture medium in the wells is replaced by a fresh one every three days, for example. The wells are then examined under a microscope for the presence of fused cells. Colonies where the presence of fused cells are observed are selected, and examined for a human immunoglobulin by, for example, radioimmunoassay using $^{125}I$, or an enzyme-linked immunosorbent assay. The selected colonies where the production of the human immunoglobulin is determined are transferred to a fresh culture medium and cultivated to proliferate the fused cells and thus obtain fused cell clones.

The serum-free culture medium containing a specific amount of retinoic acid or its salt may be advantageously utilized for cultivating human monoclonal antibody-producing human/human hybridomas. It may also be used to cultivate other hybridomas. The serum-free medium of the invention may contain a predetermined amount of retinoic acid. Alternatively, retinoic acid may be added to the medium at the time of use so that its amount may reach the above predetermined amount.

In cultivating the human monoclonal antibody-producing human/human hybridoma in the serum-free medium of the invention, the cultivation conditions may be properly selected, and if required, may be changed by performing a preliminary experiment. For example, the cultivation may be carried out at about 37±3° C. in an atmosphere containing about 5% of $CO_2$.

The following examples illustrate the preparation of the serum-free medium of the invention and the cultivation of a human monoclonal antibody-producing human/human hybridoma in the serum-free medium of the invention. It should be understood that the invention is not limited by these examples.

In the accompanying drawings,

FIG. 3 is a graph showing the results obtained in Examples 7 to 9.

EXAMPLES 1–5 AND COMPARATIVE EXAMPLE 1

Retinoic acid (commercially obtained) was used as a solution in a 0.4% aqueous solution of sodium hydroxide. A basal medium RDF for animal cell culture was used, and a serum-free complete medium was prepared by adding the following additives to the basal medium.

SERUM-FREE COMPLETE MEDIUM

| RDF basal medium | 13,433 mg/ml-complete medium |
| --- | --- |
| Transferrin | 10 μg/ml-complete medium |
| Insulin | 10 μg/ml-complete medium |
| Sodium selenite | 1 nM |
| Ethanolamine | 1 μM |
| β-Mercaptoethanol | 1 μM |
| Human albumin | 100 μg/ml-complete medium |

A serum-free medium was prepared by adding retinoic acid in each of the concentrations indicated in Table 1 to the above serum-free complete medium.

Human/human hybridoma SLNF10 (Fermentation Research Institute, Deposition Rejecting Notice No. 60-1197; human/human hybridoma capable of producing human monoclonal antibody IgG) disclosed in detail in Japanese Laid-Open Patent Publication No. 70400/1987 was washed twice with the serum-free complete medium by centrifugation at a low speed, and then inoculated in each of the serum-free complete medium (control) and the retinoic acid-containing serum-free media (Examples 1 to 5 and Comparative Example 1) at a rate of $10^5$ cells/ml and cultivated in an incubator at 37° C. in the presence of 5% of $CO_2$. Six days after the start of the cultivation, the number of cells was measured by a hemocytometer, and the amount of the antibody was measured by the following method.

Measurement of the Amount of the Antibody

An anti-human immunoglobulin antibody (100 μl) was added dropwise to a microtiter plate and adsorbed on the plate at 37° C. for 30 minutes. The plate was washed three times with 10 mM of PBS containing 0.3% of gelatin (gelatin buffer), and then 1% bovine serum albumin solution (200 μl) was added dropwise and adsorbed on the plate at 37° C. for 1 hour. The plate was washed three times with the gelatin buffer to remove the unadsorbed materials. Then, an assay sample (culture supernatant) (50 μl) was added dropwise, and reacted at 37° C. for 1 hour. The plate was washed three times with the gelatin buffer. Peroxidase-conjugated goat anti-human Ig antibody (50 μl) was added dropwise and reacted at 37° C. for 30 minutes to bind it to human Ig in the assay sample (enzyme-linked immunosorbent assay). The plate was washed three times with the gelatin buffer, and a substrate solution containing hydrogen peroxide and o-phenylenediamine was added and reacted in a dark chamber for 10 minutes. The reaction was stopped by adding 5N-$H_2SO_4$ (50 μl). The amount of the resulting yellow substrate reaction product having an absorption at 492 nm, which was proportional to the amount of human Ig in the assay sample, was measured by using an absorption photometer. By comparison with the absorbance of human Ig having a known concentration, the concentration of human Ig in the assay sample can be determined.

Figure 1:
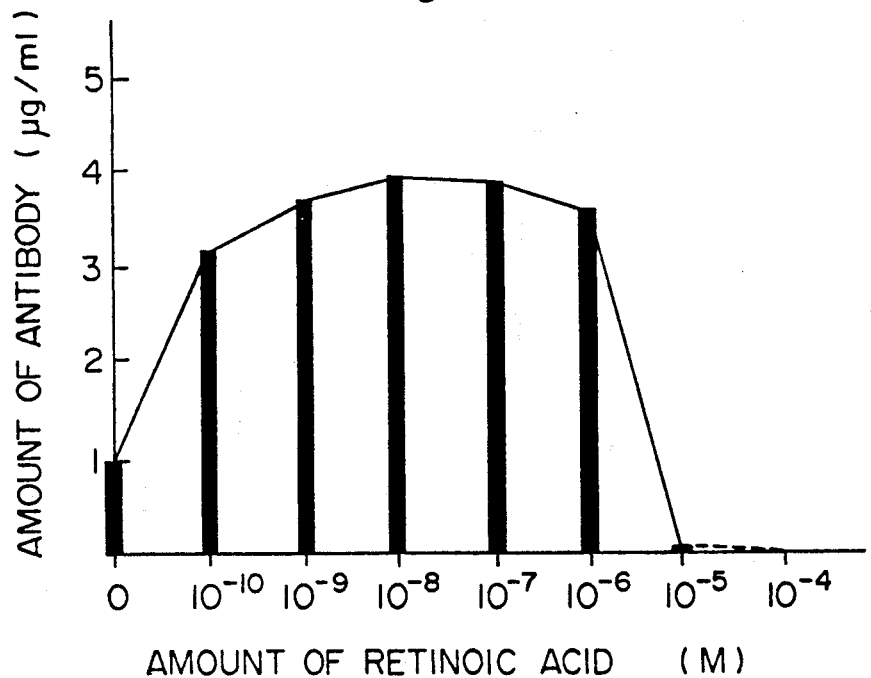
FIG. 1 is a graph showing the relationship between the amount of retinoic acid and the amount of the antibody displaced in Examples 1 to 5.

The number of cells and the amount of the antibody are shown in Table 1. FIG. 1 shows the relation between the amount of the antibody and the amount of retinoic acid.

TABLE 1

| Run | Amount of retinoic acid in the serum-free complete medium (M) | Number of cells 6 days after start of cultivation ($\times 10^6$ cells/ml) | Amount of the antibody 6 days after start of cultivation (μg/ml) |
| --- | --- | --- | --- |
| Control | 0 | 2.75 | 1 |
| Example 1 | $10^{-10}$ | — | 3.2 |
| Example 2 | $10^{-9}$ | 3.2 | 3.7 |
| Example 3 | $10^{-8}$ | — | 3.9 |
| Example 4 | $10^{-7}$ | 3.06 | 3.8 |
| Example 5 | $10^{-6}$ | — | 3.5 |
| Comparative Example 1 | $10^{-5}$ | 0.22 | (below the detection limit) |

—: Not measured

EXAMPLE 6

Subcultivation:

A serum-free medium (the medium of the invention) of the following composition was prepared.

| RDF basal medium | 13.433 mg/ml-complete medium |
| --- | --- |
| Transferrin | 10 μg/ml-complete medium |
| Insulin | 10 μg/ml-complete medium |
| Sodium selenite | 1 nM |
| β-Mercaptoethanol | 1 μM |
| L-arginine | 1 mg/ml-complete medium |
| Retinoic acid | $10^{-7}$ M |

Human/human hybridoma SLNF10 was inoculated in this serum-free medium at a rate of $10^5$ cells/ml, and its cultivation was started at 37° C. in the presence of 5% of $CO_2$. Six days layer, the first generation cells were separated from the culture broth and inoculated in a fresh serum-free medium of the same composition at a rate of $10^5$ cells/ml, and cultivated under the same cultivation conditions. Six days after the start of the second generation cultivation, the second generation cells were separated from the culture broth and inoculated in a fresh serum-free medium of the same composition at a rate of $10^5$ cells/ml, and cultivated under the same cultivation conditions.

Figure 2:
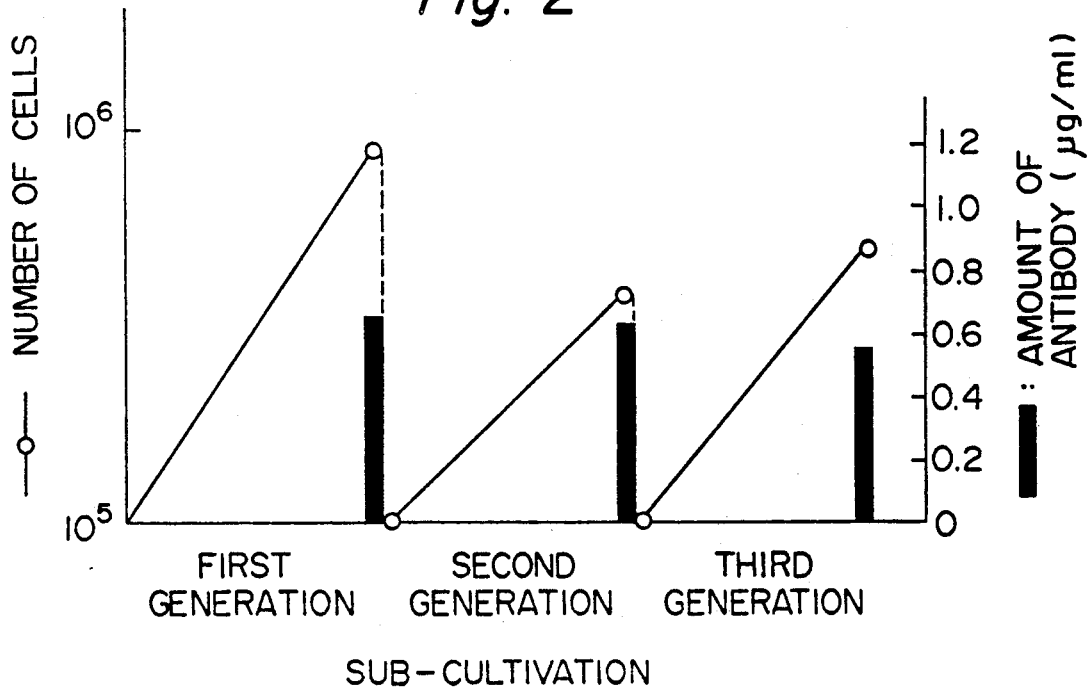
FIG. 2 is a graph showing the results obtained in Example 6 (subcultivation)

Thus, subcultivation was carried out through three generations, and the results are shown in FIG. 2. FIG. 2 demonstrates that the human monoclonal antibody IgG-producing human/human hybridoma could be cultivated for a long period of time through generations without any undesirable reduction in cell proliferating ability and antibody producibility.

EXAMPLES 7–9

In the same way as in Example 4, a serum-free medium containing no retinoic acid (control) and a serum-free medium containing $10^{-7}$ M of retinoic acid (the medium of the invention) were prepared.

The same human/human hybridoma SLNF10 as used in Example 4 and hybridomas TOS/H8 and CoLNE10 exemplified hereinabove were cultivated on these media as in Example 4. Six days after start of the cultivation, the amount of the antibody was measured. The results are shown in Table 2 and FIG. 3. IT is seen from these results that the serum-free medium of the invention can be utilized to cultivate various human/human hybridomas capable of producing human monoclonal antibodies, and a marked increase in the amount of the antibody produced can be achieved over the use of the control medium containing no retinoic acid.

TABLE 2

| Example | Human/human hybridoma | Antibody | Amount of the antibody (μg/ml) | |
| --- | --- | --- | --- | --- |
| | | | Control serum-free medium | Serum-free medium of the invention |
| 7 | SLNF10 | IgG | 0.595 | 2.38 |
| 8 | TOS/H8 | IgM | 3.80 | 9.33 |
| 9 | CoLNE10 | IgA | 4.17 | 6.60 |

What is claimed is:

1. A method of culturing a human monoclonal antibody-producing human/human hybridoma which comprises washing a human monoclonal antibody-producing human/human hybridoma with serum-free complete medium and inoculating in a second serum-free complete medium comprising at least $10^{-9}$M but not more than $10^{-6}$M of retinoic acid or its salt, and maintaining the hybridoma in the medium at a temperature and $CO_2$ atmosphere sufficient to support growth.

2. The method of claim 1, wherein the second serum-free complete medium comprises at least $10^{-9}$M but not more than $10^{-7}$M retinoic acid.

3. The method of claim 1, wherein the hybridoma is cultured at a temperature of 37° and in the presence of 5% $CO_2$.

4. The method of claim 1, wherein the second serum-free complete medium also contains at least one growth promoting additive selected from the group consisting of insulin and transferrin.

5. The method of claim 1, wherein the second serum-free complete medium comprises a basal medium for animal cell culture to which has been added complete medium-forming additives with the exception of serum, $10^{-6}$-$10^{-9}$M and retinoic acid.

6. The method of claim 5, wherein the second complete medium forming additives are selected from the group consisting of β-mercaptoethanol, selenites, ethanolamine, L-arginine, albumin, amino acids, vitamins, minerals, nucleic acid derivatives, carbohydrates, coenzymes, fatty acids and combinations thereof.

7. The method of claim 1, wherein an amount of retinoic acid in the range of $10^{-9}$-$10^{-6}$M is added to the second serum-free complete medium.

8. A method for subculturing a human monoclonal antibody-producing human/human hybridoma which comprises the steps of (1) washing the hybridoma with complete serum-free medium, (2) inoculating the hybridoma in a serum-free complete medium comprising $10^{-9}$-$10^{-6}$M retinoic acid or its salt, (3) maintaining the hybridoma in the medium at a temperature and $CO_2$ atmosphere sufficient to support growth, and for a sufficient time to generate first generation cells, (4) separating the first generation cells from the medium and inoculating these cells in fresh serum-free complete medium comprising $10^{-9}$-$10^{-6}$M retinoic acid or its salt, (5) culturing these cells under the same conditions as in step (3) and optionally repeating step (4) one or more times.

9. The method of claim 8, wherein the hybridoma is maintained at a temperature of 37° and in the presence of 5% $CO_2$.

10. A cell culture comprising a human monoclonal antibody-producing human/human hybridoma in a serum-free complete medium comprising $10^{-9}$-$10^{-6}$M retinoic acid or its salt.

11. The cell culture according to claim 10, wherein the serum-free complete medium further comprises at least one growth promoting additive selected from insulin and transferrin.

12. The cell culture according to claim 10, wherein the serum-free complete medium comprises $10^{-9}$-$10^{-7}$M retinoic acid or its salt.

13. A culture supernatant produced by culturing a human monoclonal antibody-producing human/human hybridoma in a serum-free complete medium comprising at least $10^{-9}$M but not more than $10^{-6}$M retinoic acid or its salt at a temperature and $CO_2$ atmosphere sufficient to support growth and separating the hybridoma from the medium.

14. The culture supernatant of claim 12 produced by culturing a human/human hybridoma capable of producing an IgG human monoclonal antibody in a serum-free complete medium comprising about $10^{-7}$-$10^{-9}$M retinoic acid at a temperature and $CO_2$ atmosphere sufficient to support growth and for a period of time sufficient to result in the release of about 3.7-3.9 μg/ml of human IgG to the medium and separating the hybridoma from the medium.

15. The culture supernatant of claim 12, produced by culturing a human/human hybridoma capable of producing an IgM human monoclonal antibody in a serum-free complete medium comprising $10^{-7}$M retinoic acid for a period of time sufficient for the release of about 9.3 μg/ml human IgM to the medium and separating the hybridoma from the medium.

16. The culture supernatant of claim 12, produced by culturing a human/human hybridoma capable of producing an IgA human monoclonal antibody in a serum-free complete medium comprising $10^{-7}$M retinoic acid for a period of time sufficient for the release of about 6.6 μg/ml human IgA to the medium and separating the hybridoma from the medium.

* * * * *